United States Patent [19]
Tsai

[11] Patent Number: 5,866,715
[45] Date of Patent: Feb. 2, 1999

[54] POLYCARBODIIMIDES AND METHOD FOR PRODUCING THE SAME

[75] Inventor: Fan-Cheng Tsai, Hsinchu, Taiwan

[73] Assignee: Industrial Technology Research Institute, Hsinchu, Taiwan

[21] Appl. No.: 98,145

[22] Filed: Jun. 16, 1998

[51] Int. Cl.$^6$ .................................................. C07C 331/00
[52] U.S. Cl. .............................................. 560/302; 528/78
[58] Field of Search ............................... 560/302; 528/78

[56] References Cited

U.S. PATENT DOCUMENTS 5,081,173  1/1992  Taylor ..................................... 524/195

*Primary Examiner*—Samuel Barts
*Attorney, Agent, or Firm*—Darby & Darby

[57] ABSTRACT

The present invention discloses polycarbodiimides containing two terminal hydrophilic groups, which differ from conventional polycarbodiimde crosslinkers that contain a hydrophilic portion on one side and a hydrophobic portion on the other. The polycarbodiimides have superior hydrophilic properties and crosslinking properties as well. A method for producing such polycarbodiimides is also disclosed.

20 Claims, No Drawings

POLYCARBODIIMIDES AND METHOD FOR PRODUCING THE SAME

BACKGROUND OF THE INVENTION

1. Field of the Invention

The present invention relates to polycarbodiimides and a method for producing the same. More particularly, it relates to polycarbodiimides with superior hydrophilicity and crosslinking properties.

2. Description of the Related Arts

Originally, industrial coatings were primarily solvent-borne systems, but the development of water-borne coatings has come to be of increasing interest for a number of reasons. The main reasons for the shift from solvent-borne coatings to aqueous alternatives are a decrease in the potential harm to the environment and lower toxicity. In the development of water-borne coatings, although the performance is often inferior to that of solvent-borne coatings, it is improved to a large extent by the addition of crosslinking agents such as water-dispersible polycarbodiimides.

Polycarbodiimides and their derivatives have been widely used as crosslinking agents or condensation agents in the preparation of carboxylic acids, sulfonic acids, esters, amidines, anhydrides, amides, and peptides. Previously, polycarbodiimides were prepared by reacting mercury or lead oxide with thioureas, and mercuric oxide and sodium hypochlorite were employed as catalysts later on; however, the large quantities of byproducts remained the greatest shortcoming. In recent years, polycarbodiimides were commonly obtained by heating diisocyanates at elevated temperatures by using phosphorous catalysts. Such a method has the advantages of less byproducts and a higher product yield while prolonging the reaction time. The reaction involves a combination of two isocyanate moieties to yield a carbodiimide group with evolution of carbon dioxide:

Aliphatic and aromatic carbodiimides are liquid or solid at room temperature and it is often difficult to keep them stabilized during long-term storage since they tend to dimerize and/or trimerize at temperatures as low as room temperature. The rate of dimerization and/or trimerization will be affected by the nature of the terminal group attached to each carbodiimide group.

U.S. Pat. No. 5,081,173 discloses a surface-active polycarbodiimide containing a hydrophilic portion and a hydrophobic portion joined through the reaction of a carbodiimide group with a reactive functional group. U.S. Pat. No. 5,258,481 discloses a multi-functional water-dispersible crosslinking agent which consists of oligomeric compounds containing carbodiimide functions and other reactive functional groups to improve the efficiency of the crosslinking agent. U.S. Pat. No. 5,117,059 discloses mono-disperse, multi-functional carbodiimides which provide greater reaction efficiency at lower temperatures. U.S. Pat. No. 4,072,712 discloses a method for preparing carbodiimide-isocyanate adducts. U.S. Pat. No. 5,047,588 discloses a method for preparing surface-active polycarbodiimides of the formula:

wherein X represents carbodiimide groups; R is a residue of a hydrophobic organic compound; and R' is a residue of an organic compound having a hydrophilic segment.

Generally, conventional polycarbodiimide crosslinkers contain a hydrophilic group at one end and a hydrophobic group at the opposite end. Such a structure, however, usually lacks hydrophilicity and powerful mechanical agitation is therefore required to disperse it in water. Usually, this requires the employment of special, high-shear mixing equipment, and results in the further drawback of high energy costs. Moreover, owing to the poor hydrophilicity, to guarantee a more stable dispersion, a longer hydrophobic chain is not possible, and therefore the total functional carbodiimide groups in a conventional polycarbodiimide molecular chain is restricted.

SUMMARY OF THE INVENTION

It is therefore an object of the invention to provide polycarbodiimides having superior hydrophilic properties and increased crosslinking functionality.

It is also an object of the invention to provide polycarbodiimides which can be dispersed in water by mere agitation by hand using a stirring rod, thus sparing the complicated mixing equipment.

According to a feature of the invention, two hydrophilic species with different chain lengths are incorporated onto both the ends of the polycarbodiimide, thereby forming a polycarbodiimide having two hydrophilic segments to render its hydrophilicity superior.

The polycarbodiimides according to the invention possess a tri-block structure including the hydrophobic carbodiimide backbone and two hydrophilic poly(oxyalkylene) segments, which can be represented by the following general formula I:

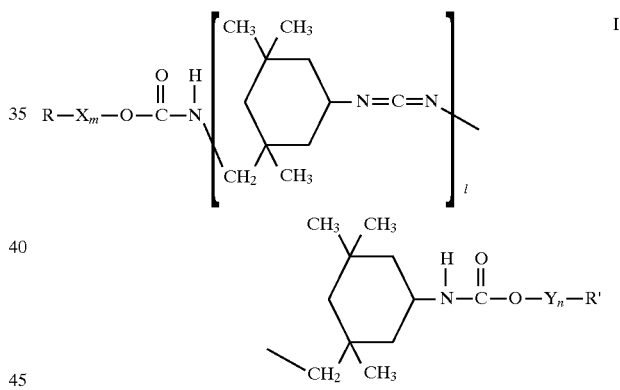

wherein the number of carbodiimide repeating unit l is an integer from 1 to 60, preferably from 1 to 40, and most preferably from 1 to 20. R—Xm— and R'—Yn— represent the two terminal hydrophilic groups of the polycarbodiimide, wherein each of X and Y, independently, is —CH$_2$CH$_2$O—, —CH$_2$CH(CH$_3$)O—, or a copolymer thereof; each of R and R', independently, is —OCH$_3$ or —OC$_2$H$_5$; m is an integer from 10 to 100, preferably from 10 to 80, and most preferably from 10 to 50; and n is an integer from 5 to 50, preferably from 5 to 40, and most preferably from 5 to 30.

Since the polycarbodiimide of the invention contains hydrophilic portions on both sides of the hydrophobic backbone, it has improved hydrophilicity and is readily dispersed in water. Furthermore, the superior hydrophilicity allows the polycarbodiimide to have a longer hydrophobic backbone in contrast to a conventional polycarbodiimide, wherein the chain length is considerably limited due to poor hydrophilicity. Accordingly, overall functionality is enhanced by the longer carbodiimide chain and the solvent resistance of the polycarbodiimide is improved as a result.

According to the invention, there is provided a method for producing polycarbodiimides comprising the steps of: (a) forming a hydrophilic-group containing adduct by reacting a diisocyanate with a first alkoxypolyalkylene glycol; (b) subjecting said hydrophilic group-containing adduct to carbodiimidization by reacting it with a further amount of said diisocyanate in the presence of a catalyst; (c) terminating said carbodiimidization by introducing a second alkoxypolyalkylene glycol, thereby forming a polycarbodiimide having two terminal hydrophilic groups.

The present invention will now be described in more detail.

Representative examples of diisocyanates as used herein include tolylene diisocyanate (TDI), isophorone diisocyanate (IPDI), diphenylmethane-4,4'-diisocyanate (MDI), hexamethylene diisocyanate (HDI), and 4,4'-dicyclohexylmethane diisocyanate ($H_{12}$MDI)

The resulting adduct of formula II then reacts with an additional amount of diisocyanate in the presence of a catalyst to proceed carbodiimidization, which forms the backbone of polycarbodiimdes. The reaction is illustrated below also by using isophorone diisocyanate as an illustration.

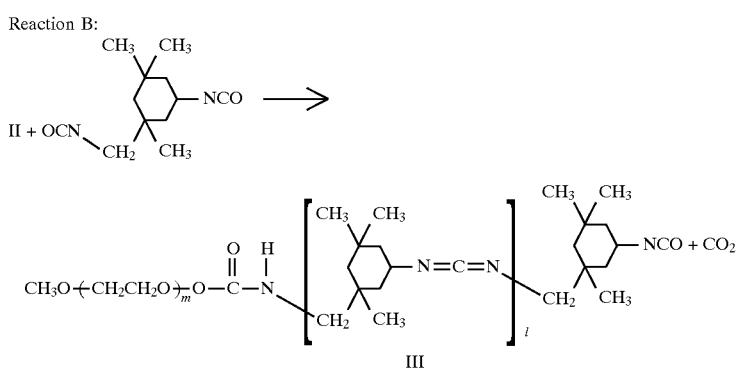

Reaction B:

DETAILED DESCRIPTION OF THE INVENTION

Polycarbodiimides of this invention can be prepared by the following synthetic reactions, A, B, and C.

According to the method of the invention, at the outset an alkoxypolyalkylene glycol is coupled to a dilsocyanate, thereby forming an isocyanate adduct which contains a hydrophilic poly(oxyalkylene) segment. When isophorone diisocyanate (IPDI) and methoxypolyethylene glycol (MPEG) are employed, the first reaction can be represented by reaction A below:

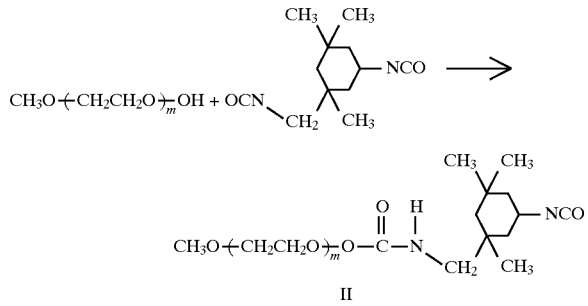

Reaction A:

This reaction is preferably performed at a temperature ranging from 30° C. to 120° C., more preferably from 40° C. to 110° C., and most preferably from 50° C. to 100° C.

This reaction is preferably performed at a temperature ranging from 100° C. to 190° C., more preferably from 110° C. to 180° C., and most preferably from 120° C. to 170° C. Catalysts suitable for use in this reaction include but are not limited to triphenyl phosphine oxide, triphenylarsine oxide, triphenylstibine oxide, tri(m-nitrophenyl)phosphine oxide, tri(m-nitrophenyl)arsine oxide, triethylphosphine oxide, 1-ethyl-3-methyl phospholine, and 3-methyl-1-phenyl-2-phospholene-1-oxide. The reaction can be carried out in a non-reactive solvent if necessary. Solvents suitable for use in this reaction should not possess active hydrogens such as would react with the isocyanate starting material or the carbodiimide adduct. Exemplary solvents include: ethyl acetate, isopropyl acetate, butyl acetate, amyl acetate, butyl phthalate, N-methyl pyrrolidone, methyl cellosolve acetate, butyl cellosolve acetate, carbitol acetate, butyl carbitol acetate, glyceryl triacetate, hexylene glycol diacetate, methyl ethyl ketone, diethyl ketone, methyl isobutyl ketone, isophorone, cyclohexanone, isopropanol, and isobutanol. The non-reactive solvent preferably constitutes about 10–70 percent by weight of all reactants, more preferably about 20–60 percent, most preferably about 30–50 percent.

When reaction B, i.e., the carbodiimidization, approaches its theoretical completion, a second alkoxypolyalkylene glycol, e.g., methoxypolyethylene glycol, is added to terminate the reaction (see reaction C below). Consequently, a second hydrophilic group is grafted onto the carbodiimide intermediate, thus obtaining a polycarbodiimide with two terminal hydrophilic segments.

Reaction C:

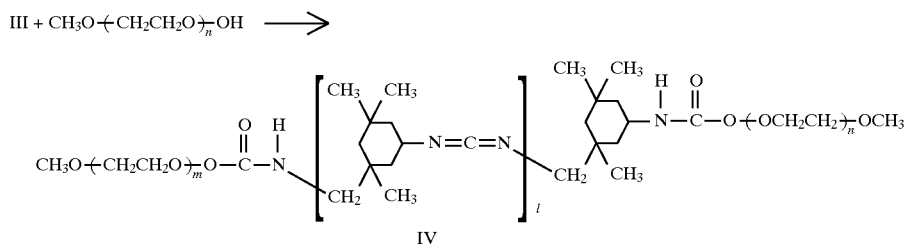

This reaction can be affected at a temperature ranging from 60° C. to 150° C., more preferably from 70° C. to 140° C., and most preferably from 80° C. to 130° C. According to the method of the invention, the two alkoxypolyalkylene glycols employed in reaction A and reaction C can be the same or different and are preferably alkoxypolyethylene glycol, alkoxypolypropylene glycol, or a copolymer thereof. Preferred alkoxypolyalkylene glycols for reaction A include about 10–100 repeating units selected from —$CH_2CH_2O$— or —$CH_2CH(CH_3)O$—, or a copolymer thereof and the number of repeating units is more preferably within the range of about 10–80, and most preferably within the range of about 10–50. Preferred alkoxypolyalkylene glycols for reaction C include about 5–50 repeating units selected from —$CH_2CH_2O$— or —$CH_2CH(CH_3)O$—, or a copolymer thereof and the number of repeating units is more preferably within the range of about 5–40, and most preferably within the range of about 5–30.

The invention is described in greater detail with reference to the following non-limiting examples.

EXAMPLE 1

This example illustrates the preparation of a polycarbodiimide of formula IV.

Into a four-neck reactor were charged 110 g of methoxy-polyethylene glycol (MPEG) and 44.4 g of isophorone diisocyanate (IPDI), and the resulting mixture was heated at 70° C. for a short period. Subsequently, additional 177.6 g of IPDI and 0.8 g of 3-methyl-1-phenyl-2-phospholene-1-oxide and 62 g of amyl acetate were added, and the reaction temperature was raised to 140° C. in order to subject the reactants to carbodiimidization. The reaction was continued for 20 hours. Then, 140 g of MPEG was further added and the reaction mixture was heated at 100° C. for 2 hours to give a polycarbodiimide of formula IV.

The polycarbodiimide thus obtained was mixed with water-dispersible polyurethane (50UD, Bayer Co.,) and the resulting dispersion was coated on a steel board and cured to give a thin film. The resulting film was tested for solvent resistance by a ASTM D4752-87 standard test. A piece of cheesecloth in which a 1 kg plumb was wrapped, was saturated with methyl ethyl ketone (MEK), then rubbed on the substrate until the coating was penetrated. One back-and-forth rub is a double rub. The polycarbodiimide was also dispersed in water to evaluate the dispersibility, particle size, and precipitation property. The particle size was determined by using a submicron particle sizer (NICOMP model 270). The testing results of MEK double rubs and the water-dispersibility are shown in Table 1.

EXAMPLE 2

The procedure outlined in Example 1 was repeated with the exception that the amount of IPDI used in the carbodiimidization was changed to 222 g. The testing results of MEK double rubs and the water-dispersibility are shown in Table 1.

EXAMPLE 3

The procedure of Example 1 was repeated with the exception that the used amount of IPDI in the carbodiimidization was changed to 266.4 g. The testing results of MEK double rubs and the water-dispersibility are shown in Table 1.

EXAMPLE 4

The procedure of Example 1 was repeated with the exception that the amount of IPDI used in the carbodiimidization was changed to 310.8 g. The testing results of MEK double rubs and the water-dispersibility are shown in Table 1.

EXAMPLE 5

The procedure of Example 1 was repeated with the exception that the amount of IPDI used in the carbodiimidization was changed to 355.2 g. The testing results of MEK double rubs and the water-dispersibility are shown in Table 1.

COMPARATIVE EXAMPLE

The commercially available polycarbodiimide (made by Union Carbide Corporation; trade name: XL-29SE) was evaluated for water-dispersibility and resistance to MEK double-rubs by repeating the same testing procedures of Example 1 and the results are shown in Table 1 below.

TABLE 1

|  | EX. 1 | EX. 2 | EX. 3 | EX. 4 | EX. 5 | XL-29SE |
|---|---|---|---|---|---|---|
| MEK Double Rubs (times) | | | | | | |
| 3% | 75 | 110 | 120 | 120 | 120 | 71 |
| 5% | 83 | 130 | 128 | 125 | 125 | 80 |
| Water dispersibilty | Acceptable | Acceptable | Acceptable | Acceptable | Acceptable | Acceptable |
| Particle size($\mu$m) | 35 | 40 | 90 | 145 | 160 | 80 |
| Precipitation on the next day | No | No | No | No | No | Yes |

As shown in Table 1, the polycarbodiimide of Comparative Example precipitates on the second day while those of Examples 1–5 remain dispersed in water, which means the polycarbodiimides of the invention have better hydrophilicity and water-dispersibility. Moreover, the polycarbodiimides of the invention give more satisfactory results in the double-rubs tests, suggesting they have higher crosslinking functionalities than conventional ones.

What is claimed is:

1. A polycarbodiimide of the formula:

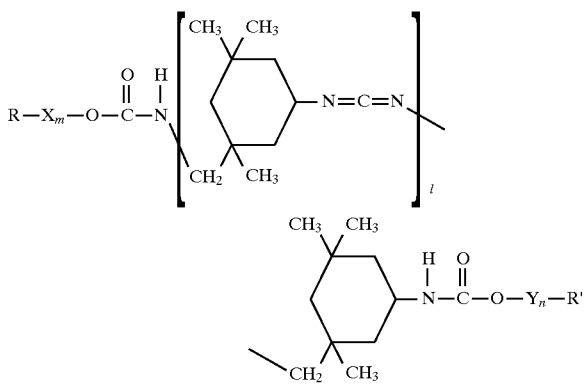

wherein
each of X and Y, independently, is —CH$_2$CH$_2$O—, —CH$_2$CH(CH$_3$)O—, or a copolymer thereof;
each of R and R', independently, is —OCH$_3$ or —OC$_2$H$_5$;
l is an integer from 1 to 60;
m is an integer from 10 to 100; and
n is an integer from 5 to 50.

2. The polycarbodiimide of claim 1, wherein l is an integer from 1 to 40; m is an integer from 10 to 80; and n is an integer from 5 to 40.

3. The polycarbodiimide of claim 2, wherein l is an integer from 1 to 20; m is an integer from 10 to 50; and n is an integer from 5 to 30.

4. The polycarbodiimide of claim 1, wherein each of X and Y is —CH$_2$, CH$_2$O—; and each of R and R', is —OCH$_3$.

5. The polycarbodiimide of claim 4, wherein l is an integer from 1 to 40; m is an integer from 10 to 80; and n is an integer from 5 to 40.

6. The polycarbodiimide of claim 5, wherein l is an integer from 1 to 20; m is an integer from 10 to 50; and n is an integer from 5 to 30.

7. A method for producing polycarbodiimides, comprising the steps of:
(a) forming a hydrophilic-group containing adduct by reacting a diisocyanate with a first alkoxypolyalkylene glycol;
(b) subjecting said hydrophilic group-containing adduct to carbodiimidization by reacting it with a further amount of said diisocyanate in the presence of a catalyst;
(c) terminating said carbodiimidization by introducing a second alkoxypolyalkylene glycol, thereby forming a polycarbodiimide having two terminal hydrophilic groups.

8. The method of claim 7, wherein said diisocyanate is selected from the group consisting of tolylene diisocyanate, isophorone diisocyanate, diphenylmethane-4,4'-diisocyanate, hexamethylene diisocyanate, and 4,4'-dicyclohexylmethane diisocyanate.

9. The method of claim 7, wherein the first alkoxypolyalkylene glycol and the second alkoxypolyalkylene glycol are independently the same or different and represent alkoxypolyethylene glycol, alkoxypolypropylene glycol, or a copolymer thereof.

10. The method of claim 7, wherein the first alkoxypolyalkylene glycol and the second alkoxypolyalkylene glycol, respectively, include about 10–100 and about 5–50 repeating units selected from —CH$_2$CH$_2$O—, —CH$_2$CH(CH$_3$)O—, or a copolymer thereof.

11. The method of claim 10, wherein the first alkoxypolyalkylene glycol and the second alkoxypolyalkylene glycol, respectively, include about 10–80 and about 5–40 repeating units selected from —CH$_2$CH$_2$O—, —CH$_2$CH(CH$_3$)O—, or a copolymer thereof.

12. The method of claim 10, wherein the first alkoxypolyalkylene glycol and the second alkoxypolyalkylene glycol, respectively, include about 10–50 and about 5–30 repeating units selected from —CH$_2$CH$_2$O—, —CH$_2$CH(CH$_3$)O—, or a copolymer thereof.

13. The method of claim 7, wherein the catalyst is selected from the group consisting of triphenyl phosphine oxide, triphenylarsine oxide, triphenylstibine oxide, tri(m-nitrophenyl)phosphine oxide, tri(m-nitrophenyl)arsine oxide, triethylphosphine oxide, 1-ethyl-3-methyl phospholine, and 3-methyl-1—phenyl-2—phospholene-1—oxide.

14. The method of claim 7, wherein said carbodiimidization is carried out in a non-reactive solvent selected from the group consisting of ethyl acetate, isopropyl acetate, butyl acetate, amyl acetate, butyl phthalate, N-methyl pyrrolidone, methyl cellosolve acetate, butyl cellosolve acetate, carbitol acetate, butyl carbitol acetate, glyceryl triacetate, hexylene glycol diacetate, methyl ethyl ketone, diethyl ketone, methyl isobutyl ketone, isophorone, cyclohexanone, isopropanol, and isobutanol.

15. The method of claim 14, wherein said non-reactive solvent constitutes 10–70 percent by weight of all reactants.

16. The method of claim 15, wherein said non-reactive solvent constitutes 20–60 percent by weight of all reactants.

17. The method of claim 16, wherein said non-reactive solvent constitutes 30–50 percent by weight of all reactants.

18. The method of claim 7, wherein the reactions of the steps (a), (b), and (c) are performed at temperatures of about 30°–120° C., 100°–190° C., and 60°–150° C. respectively.

19. The method of claim 18, wherein the reactions of the steps (a), (b), and (c) are performed at temperatures of about 40°–110° C., 110°–180° C., and 70°–140° C. respectively.

20. The method of claim 19, wherein the reactions of the steps (a), (b), and (c) are performed at temperatures of about 50°–100° C., 120°–170° C., and 80°–130° C. respectively.

* * * * *

UNITED STATES PATENT AND TRADEMARK OFFICE
CERTIFICATE OF CORRECTION

PATENT NO. : 5,866,715
DATED : February 2, 1999
INVENTOR(S) : Fan-Cheng TSAI

It is certified that error appears in the above-identified patent and that said Letters Patent is hereby corrected as shown below:

On the title page, insert

--[30]  Foreign Application Priority Data

December 17, 1997  TAIWAN .......... 86119127--.

Signed and Sealed this

Thirteenth Day of July, 1999

Attest:

Q. TODD DICKINSON

Attesting Officer  Acting Commissioner of Patents and Trademarks